(12) United States Patent
Cowan et al.

(10) Patent No.: US 8,494,637 B2
(45) Date of Patent: *Jul. 23, 2013

(54) SYSTEMS AND METHODS FOR IMPLANTABLE LEADLESS GASTROINTESTINAL TISSUE STIMULATION

(75) Inventors: Mark W. Cowan, Fremont, CA (US);
Richard E. Riley, Palo Alto, CA (US);
Axel F. Brisken, Fremont, CA (US);
Debra S. Echt, Woodside, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 207 days.

This patent is subject to a terminal disclaimer.

(21) Appl. No.: 13/008,521

(22) Filed: Jan. 18, 2011

(65) Prior Publication Data

US 2011/0112600 A1    May 12, 2011

Related U.S. Application Data

(62) Division of application No. 11/764,583, filed on Jun. 18, 2007, now Pat. No. 7,899,541.

(60) Provisional application No. 60/805,316, filed on Jun. 20, 2006.

(51) Int. Cl.
*A61N 1/08* (2006.01)
(52) U.S. Cl.
USPC .............................................. 607/40; 607/60
(58) Field of Classification Search
USPC ..................................................... 607/40, 60
See application file for complete search history.

(56) References Cited

U.S. PATENT DOCUMENTS

| | | | |
|---|---|---|---|
| 3,411,507 A | 11/1968 | Wingrove | |
| 5,423,872 A | 6/1995 | Cigaina | |
| 5,876,425 A * | 3/1999 | Gord et al. | 607/56 |
| 6,037,704 A | 3/2000 | Welle | |
| 6,321,124 B1 | 11/2001 | Cigaina | |
| 6,366,816 B1 | 4/2002 | Marchesi | |
| 6,535,764 B2 | 3/2003 | Imran et al. | |
| 7,054,689 B1 | 5/2006 | Whitehurst et al. | |

(Continued)

FOREIGN PATENT DOCUMENTS

DE    4330680 A1    3/1995

OTHER PUBLICATIONS

Office action dated Jun. 9, 2010 for U.S. Appl. No. 11/764,583.
Office action dated Jun. 16, 2009 for U.S. Appl. No. 11/764,583.

(Continued)

*Primary Examiner* — Eric D. Bertram
(74) *Attorney, Agent, or Firm* — Wilson, Sonsini, Goodrich & Rosati

(57) ABSTRACT

Systems and methods are disclosed to stimulate gastrointestinal tissue to treat medical conditions such as eating disorders, gastroparesis, and gastric reflux. The invention uses electrical stimulation of the nerve, where vibrational energy from a source is received by an implanted device and converted to electrical energy and the converted electrical energy is used by implanted electrodes to stimulate the pre-determined gastrointestinal tissue site. The vibrational energy is generated by a controller-transmitter, which could be implanted or located externally. The vibrational energy is received by a receiver-stimulator, which could be located in the various regions on or around the gastrointestinal tissue that needs to be stimulated. The implantable receiver-stimulator stimulates different gastrointestinal tissue to provide the desired therapeutic benefit.

11 Claims, 6 Drawing Sheets

U.S. PATENT DOCUMENTS

| | | |
|---|---|---|
| 7,054,690 B2 | 5/2006 | Imran |
| 7,899,541 B2 | 3/2011 | Cowan et al. |
| 2004/0172083 A1* | 9/2004 | Penner .......................... 607/35 |
| 2004/0204744 A1 | 10/2004 | Penner et al. |
| 2006/0136004 A1 | 6/2006 | Cowan et al. |

OTHER PUBLICATIONS

Office action dated Oct. 17, 2008 for U.S. Appl. No. 11/764,583.

Office action dated Nov. 2, 2009 for U.S. Appl. No. 11/764,583.

* cited by examiner

SYSTEMS AND METHODS FOR IMPLANTABLE LEADLESS GASTROINTESTINAL TISSUE STIMULATION

CROSS-REFERENCES TO RELATED APPLICATIONS

The present application is a divisional of U.S. Pat. No. 7,899,541, filed Jun. 18, 2007, which claims the benefit of provisional U.S. Application No. 60/805,316 filed Jun. 20, 2006, the full disclosures of which are incorporated herein by reference.

BACKGROUND OF THE INVENTION

1. Field of the Invention

The systems and methods of this invention relate to direct electrical stimulation of the gastrointestinal system of the body as a treatment for a variety of medical conditions. Specifically, the present invention relates to methods and apparatus for applying such stimulation to selected portions of the gastrointestinal system without the use of conventional lead/electrode systems.

2. Description of the Background Art

Electrical stimulation of the gastrointestinal system or gastrointestinal tract for the purpose of controlling gastrointestinal activity has been known and actively practiced for several decades. Application of an electrical field between electrodes to gastrointestinal tissue is known to affect the motility and electromotor conduct of the gastric tract; for example, it has been used in the treatment of eating disorders (e.g., obesity, thinness, bulimia, anorexia). For example, applying specific electrical pulses to the selected areas of the stomach can induce a sense of satiety. Disturbances in electromotor activity in diabetic gastroparesis, reflux in the upper digestive tract, and numerous other gastroenterological functional pathologies can be observed with electrophysiologic sensing and also treated with application of electrical stimulation. Electrical stimulation of other locations in the tract can induce voiding or can be used as a treatment for gastric reflux. These applications are currently practiced using both implanted and externally applied devices.

Depending on the individual patient, gastrointestinal stimulation can effectively modify signal pathways along the tract and thus provide relief of symptoms or control of bodily function. Treatment regimens and targeted gastrointestinal tissue locations are known in related art through use of current, common stimulation devices and methods. Currently, implanted devices for gastrointestinal tissue stimulation are made by companies such as IntraPace and Transneuronix.

As illustrated in FIG. 1a, the gastrointestinal system is essentially a long tube running from the mouth to the anus consisting of four main sections including the oesophagus, the stomach, the small intestines, and the large intestines. These specialized sections are capable of digesting material place in the mouth and extracting components useful to the body as the material passes through the system. Material that can not be used or that has been processed is expelled from the end of the tube at the anus. The system is under hormonal control, with the presence of food in the mouth triggering off a cascade of hormonal actions; when there is food in the stomach, different hormones activate acid secretion, increased gut motility, enzyme release etc. As illustrated in FIG. 1b, the stomach is a 'j'-shaped organ, with two openings—the esophageal and the duodenal, and four regions—the cardia, fundus, body and pylorus. Each region performs different functions; the fundus collects digestive gases, the body secretes pepsinogen and hydrochloric acid, and the pylorus is responsible for mucus, gastrin and pepsinogen secretion. The body uses this arrangement to process food and supply nutrients to the system.

In one early application of electrical gastrointestinal tissue stimulation, an electrode was passed down the esophagus to the stomach and electrical stimulation applied between the electrode and an electrode placed on the patient's abdomen. This induced peristaltic activity within the system. This was an external application of the electrical stimulation system. More recently, the concept has been extended to apply an implantable system into the stomach either as a self-contained stimulator or with electrodes on leads attached to the stomach and then connected to a subcutaneous implanted pulse generator. These systems have been found useful in treatment of obesity both for improving motility in patients and for providing a feeling of satiety to reduce intake.

In the context of this application, Gastrointestinal Tissue Stimulation (GTS) refers to treatments for a variety of medical conditions that apply electrical stimulation directly to gastrointestinal tissues. Currently available stimulator systems for GTS are fully implanted electronic devices placed within the stomach or placed subcutaneously under the skin and connected via insulated metal lead(s) to electrodes which are invasively inserted into, around, or onto gastrointestinal tissue. An implanted GTS system contains a battery to power the system. Some implanted GTS systems use an RF wireless connection instead of a battery to power the implanted device. In these RF systems, a receiver device is implanted subcutaneously and a transmitter is worn on the outside of the body. The antenna are tuned to each other and aligned such that control information and power is transmitted to the receiver and then directs the electrical impulses to the electrodes through the leads. The external transmitter contains batteries to power the transmission. All systems have the capability to externally adjust settings of the implanted system through a programming device.

In some GTS systems, electrical energy is delivered through lead wires to the electrodes; in other applications, the self-contained devices incorporate a battery with electrodes disposed on the outer surfaces of the device. For GTS, implanted electrodes are positioned on, around, or in close proximity to the gastrointestinal tissue to be stimulated. GTS uses the implanted electrodes to deliver a variety of stimulation modalities for propagation along the gastrointestinal tissue with the electric pulse waveform defined by a plurality of variables, including: pulse width, pulse frequency (Hz) or duty cycle, amplitude (V), and waveform shape (e.g., monophasic or bi-phasic).

GTS is used for treatment of motor disorders of the stomach, such as duodenogastric and gastroesophageal refluxes and relapsing duodenal peptic disorders (ulcer or phlogosis); and for treating obesity and other syndromes related to motor disorders of the stomach.

As described above, GTS devices are battery-powered electronic devices implanted and often connected via insulated metal lead(s) to electrodes which are either placed on the stomach or in the stomach or otherwise within or on the gastrointestinal tissues selected for stimulation. The implanted electrodes for GTS are positioned on leads that may be placed percutaneously, through needle punctures, or through minimally invasive surgical procedures such as laparoscopic methods, or through direct surgical access to position the electrodes on, around, or in proximity to the targeted gastrointestinal tissue. The implanted leads are then subcutaneously tunneled to the pulse generator (also referred to as a controller) that is implanted in a subcutaneous pocket. The use of these lead wires is associated with significant problems such as complications due to infection, lead failure, lead migration, and electrode/lead dislodgement. Application of electrodes to the gastrointestinal tissues can be difficult, because the stomach is uniquely designed to pass material through the system; consequently, electrodes are often expelled through the system itself.

Other prior art has attempted to deal with the complications and limitations imposed by the use of electrical leads. For example, self-contained implantable microstimulators and remotely powered microstimulators implanted through the esophagus into gastrointestinal tissue have been described; however, each approach suffers from some significant limitation. A self-contained microstimulator must incorporate a battery or some other power supply; this imposes constraints on size, device lifetime, available stimulation energy, or all three.

For leadless solutions in other similar stimulation applications, remotely powered devices have previously utilized either radiofrequency (RF) or electromagnetic transformer power transmission. RF energy transmission, unless the transmitting and receiving antennae are placed in close proximity, suffers from inefficiency and limited safe power transfer capabilities, limiting its usefulness in applications where recharging or stimulation must be accomplished at any significant depth (>1-2 cm) within the body, in particular where it is desired to permanently implant both the transmitter and receiver-stimulator. Electromagnetic coupling can more efficiently transfer electrical power, and can safely transfer higher levels of power (devices with capacity in excess of 20 Watts have been produced), but again relies on close proximity between transmitting and receiving coils, or the utilization of relatively large devices for deeper (5-8 cm maximum) implantation.

The methods and apparatus of the current invention utilize vibrational energy, particularly at ultrasonic frequencies, to overcome many of the limitations of currently known solutions for selected gastrointestinal tissue stimulation, by achieving a gastrointestinal tissue stimulation capability without the use of leads connected to a stimulation controller/pulse generator. It is not the intent to limit the scope of this invention to the gastrointestinal tissues in the description but rather to provide a broad solution for stimulation of any selected gastrointestinal tissue without the use of leads.

The following patents, all of which are incorporated in this disclosure in their entirety, describe various aspects of using electrical stimulation for achieving various beneficial effects by selected gastrointestinal tissue stimulation. U.S. Pat. No. 3,411,507 titled "Method of Gastrointestinal Stimulation with Electrical Pulses" by Wingrove describes an application for stimulation of the stomach with an external stimulator and a lead placed down the throat into the stomach. U.S. Pat. No. 7,054,690 titled "Gastrointestinal stimulation device" by Imran describes fixation of electrodes in an implantable application for stimulation of the gastrointestinal tissue as a treatment for obesity or other control of stomach function. U.S. Pat. No. 6,535,764 titled "Gastric treatment and diagnosis device and method" by Imran et al. describes an implantable application for stimulation and devices for attaching electrodes to the stomach. U.S. Pat. No. 6,321,124 titled "Implant device for electrostimulation and/or monitoring of endo-abdominal cavity tissue" by Cigaina describes an implantable application for stimulation of the gastrointestinal tissue as a treatment for a variety of digestive disorders and electromotor control of the intestines. U.S. Pat. No. 5,423,872 titled "Process and device for treating obesity and syndromes related to motor disorders of the stomach of a patient" by Cigaina describes an implantable application for stimulation of the gastrointestinal tissue as a treatment for obesity. U.S. Pat. No. 7,054,689 titled "Fully implantable neurostimulator for autonomic nerve fiber stimulation as a therapy for urinary and bowel dysfunction" by Whitehurst et al. describes an implantable microstimulator used generally for stimulation of gastrointestinal tissue. U.S. Pat. No. 6,037,704 titled "Ultrasonic Power Communication System" by Welle describes the use of ultrasound energy transfer from a transmitter to a receiver for purposes of powering a sensor or actuator without being connected by a lead/wire. U.S. Pat. No. 6,366,816 titled "Electronic Stimulation Equipment with Wireless Satellite Units" by Marchesi describes a tissue stimulation system based on a wireless radio transmission requiring the charging of a battery at the receiver and separate command signals used to control the delivery of stimulation. German patent application DE4330680A1 titled "Device for Electrical Stimulation of Cells within a Living Human or Animal" by Zwicker describes a general approach to power transfer using acoustic energy for tissue stimulation.

BRIEF SUMMARY OF THE INVENTION

This invention relates to methods and devices for using electrical stimulation of gastrointestinal tissues as a treatment and as a relief of symptoms or control of gastrointestinal function. This invention uses vibrational energy as a means to transmit energy and signal information from a first device, to a second device containing means to receive such vibrational energy and converting it into electrical energy and then apply that electrical energy to stimulating electrodes. The first device is intended to be either implanted or to be used externally. The second device is intended to be either permanently or temporarily implanted with stimulating electrodes in contact with or in close proximity to the specific gastrointestinal tissue to be stimulated.

This application of leadless electrical stimulation is for specific gastrointestinal tissue applications. The invention is a system comprising a controller-transmitter, an implanted receiver-stimulator, a programmer to adjust therapy parameters, and stimulation electrodes, such that the stimulation electrodes would be in contact with gastrointestinal tissue or in close proximity to the gastrointestinal tissue to be stimulated to facilitate treatment. Systems incorporating the concepts presented have significant advantages over currently available devices, particularly by eliminating the requirement for electrical leads, or eliminating the requirement for self-contained battery supply within a microstimulator, and by providing the capability for simultaneous or sequenced stimulation of multiple sites.

In one embodiment, the controller-transmitter is implanted. The controller-transmitter is implanted subcutaneously beneath the skin. In another embodiment, the controller-transmitter is located on the patient's body or surface of the skin. The transmitted vibrational energy is directed to the receiver-stimulator to cause electrical stimulation at the electrodes of the receiver-stimulator.

In one use of the external embodiment of the controller-transmitter, the device is for fecal incontinence, in another use the external embodiment is for treating obesity. In the external embodiment, miniaturized receiver-stimulator devices are implanted, but the controller-transmitter unit is external to the body, possibly hand-held or worn attached to a belt or harness. The acoustic energy from the external controller-transmitter is coupled through the skin as well as any underlying gastrointestinal tissues, to the implanted device. The external controller-transmitter is under control of the patient. Thus, for examples, when the patient begins to feel discomfort, or the patients feels hungry, the controller-transmitter unit is applied and/or switched on, and certain characteristics, for example, the level of stimulating energy and possibly the frequency or pulse duration of the stimulating waveform, is modified by the user, enabling the user to tailor the stimulation as needed.

DETAILED DESCRIPTION OF THE INVENTION

Figure 1B:
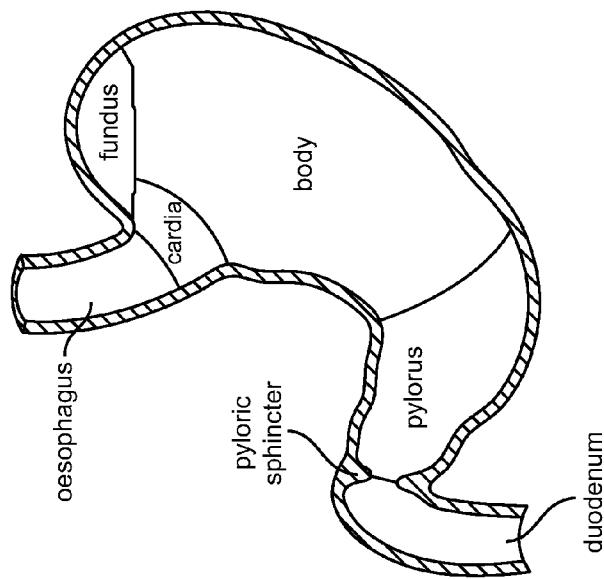
FIGS. 1a and 1b are schematics showing the basics of the gastrointestinal system anatomy.
Figure 1A:
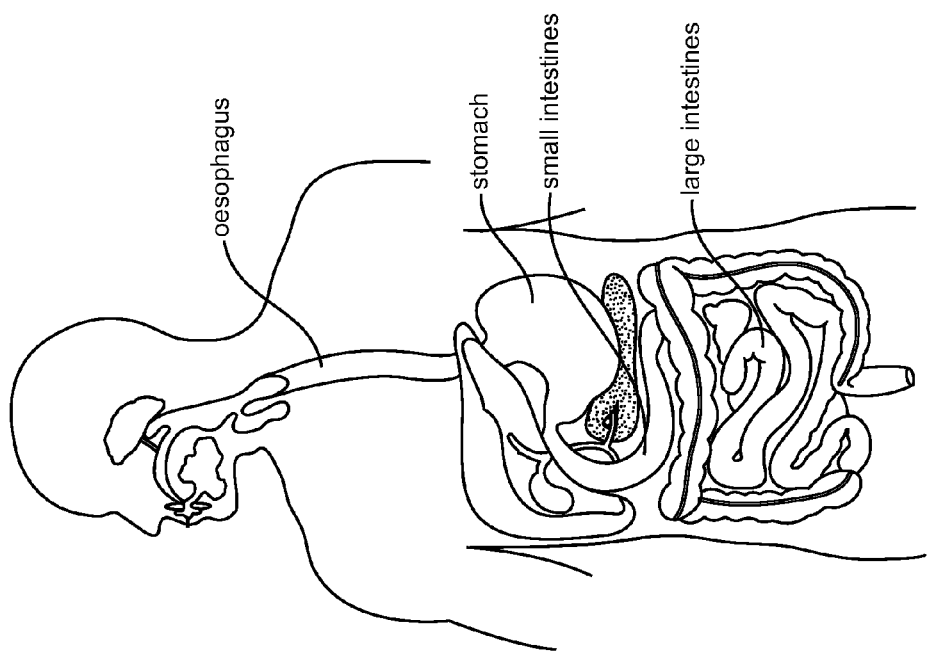

The systems and devices described here comprise a controller-transmitter device that will deliver vibrational energy and information to one or more implanted receiver-stimulator device(s) that will convert the vibrational energy to electrical energy of a form that can be used to electrically stimulate gastrointestinal tissue. The vibrational energy can be applied with ultrasound as a single burst or as multiple bursts or as a continuous wave with appropriate selection of the following parameters:

| Parameter | Value Range |
|---|---|
| Ultrasound frequency | 20 kHz-10 MHz |
| Burst Length (#cycles) | 3-Continuous |
| Stimulation Pulse Duration | 0.1 µsec-Continuous |
| Duty Cycle | 0-100% |
| Mechanical Index | ≦1.9 |

The controller-transmitter device would contain one or more ultrasound transducers of appropriate size(s) and aperture(s) to generate sufficient acoustic power to achieve the desired stimulation at the location of an implanted receiver-stimulator device. Additionally, multiple implanted receiver-stimulator devices may be placed within the region insonified by the controller-transmitter device. Multiple receiver-stimulator implants may function simultaneously; it is also possible for multiple devices to function independently, either by responding only to a specific transmitted frequency, or through the use of a selective modulation technique such as pulse width modulation, or through encoding techniques such as time-division multiplexing.

A leadless receiver-stimulator would be placed using transesophageal, percutaneous or direct surgical access. For the transesophageal approach, an endoscopy style device swallowed by the patient can be used to access the gastrointestinal system and the receiver-stimulator could be placed in the desired location. Alternatively, a percutaneous needle or laparoscopic delivery technique is used to access the gastrointestinal tissue, a miniaturized receiver-stimulator device, disposed within the delivery needle or within the laparoscopy device, is implanted into gastrointestinal tissue or attached to the desired location on the external surface of gastrointestinal tissue. Currently known techniques and tools for surgical access and probing of gastrointestinal tissue could be adapted to facilitate delivery of the receiver-stimulator to these locations; the receiver-transmitter may incorporate means to provide permanent attachment to the implant site including possibly helical coils, clips, barbs, tines, or the like or would be adapted in form to surround the gastrointestinal tissue as a wrap or along the length of the gastrointestinal tissue.

Functionally, the receiver-stimulator device comprises an ultrasound transducer to receive acoustic energy and transform it into electrical energy, an electrical circuit to transform the alternating electrical energy into direct current, and electrodes to transfer the electrical field energy between an electrode pair to the gastrointestinal tissue.

Additionally, a controller-transmitter device is adapted for directional, vibrational energy transmission emitted by the device to intersect the implanted receiver-stimulator. In an implanted version, the controller-transmitter device containing the transmitting transducer is implanted typically just beneath the skin in a subcutaneous space. If not implanted, the transducer portion of the transmitter would be placed on the skin directionally angled to the target region containing the receiver-stimulator with acoustic gel, or other means, used for coupling the acoustic energy to the skin.

In an alternative embodiment, the controller-transmitter device is incorporated into a device also providing conventional lead-based electrical stimulation, in a gastrointestinal tissue stimulation system wherein a conventional lead/electrode system would provide stimulus to directly connected regions of the gastrointestinal tissue using leads and transmitting vibrational energy to provide stimulation to regions of the gastrointestinal tissue where receiver-stimulators are implanted.

The controller-transmitter device would contain similar elements of most currently available stimulator systems, including a power source, stimulation control and timing circuitry, physiologic sensing systems; and in the implanted embodiment, a system to communicate with an outside console for data transmission, diagnostic, and programming functions typically through a radiofrequency (RF) link is provided. Additionally, the controller-transmitter device would contain an ultrasound amplifier and one or more ultrasound transducers to generate acoustic energy, and transmit such energy in the general direction of the receiver-stimulator implanted in the body. The duration, timing, and power of the acoustic energy transmission would be controlled as required, per tested parameters that are constructed for specific treatments.

A single receiver-stimulator device is implanted with the electrodes in contact or close proximity to the gastrointestinal tissue, as described above, for single-region stimulation; alternatively, it would be possible to implant a plurality of receiver-stimulator devices to stimulate either simultaneously by receiving the same transmitted acoustic energy or independently by responding only to acoustic energy of a specific character (i.e., of a certain frequency, amplitude, or by other modulation or encoding of the acoustic waveform) intended to energize only that specific device. This enables a much more robust utilization of site and region specific stimulation not currently practical with current lead-based implementations whose electrode spacing is fixed on the lead set selected for use and may not adapt itself to the structure of the gastrointestinal tissue. Selecting multiple sites and regions for treatments would be greatly enhanced by eliminating the need to connect multiple electrode sites to the stimulation energy source by the use of multiple leads/wires connected to the electrodes or by attempting to anticipate the required spacing between electrodes.

These examples are representative, and in no way limiting the applications in which an electro-acoustic stimulator based on this invention may be utilized to stimulate specific gastrointestinal tissues in the body to treat symptoms or control bodily functions.

The delivery of ultrasound energy and, therefore, electrical stimulation could either be automatically triggered based on information received from an internal or external physiological sensor, or be based upon programmed settings, or be manually activated by the patient or other individuals. More specifically, the timing of the initiation of the delivery and/or the duration of the delivery and/or the energy content of the delivery and/or the information content of the delivery could be based upon sensor information or based upon programmed settings or be manually controlled.

Figure 2:
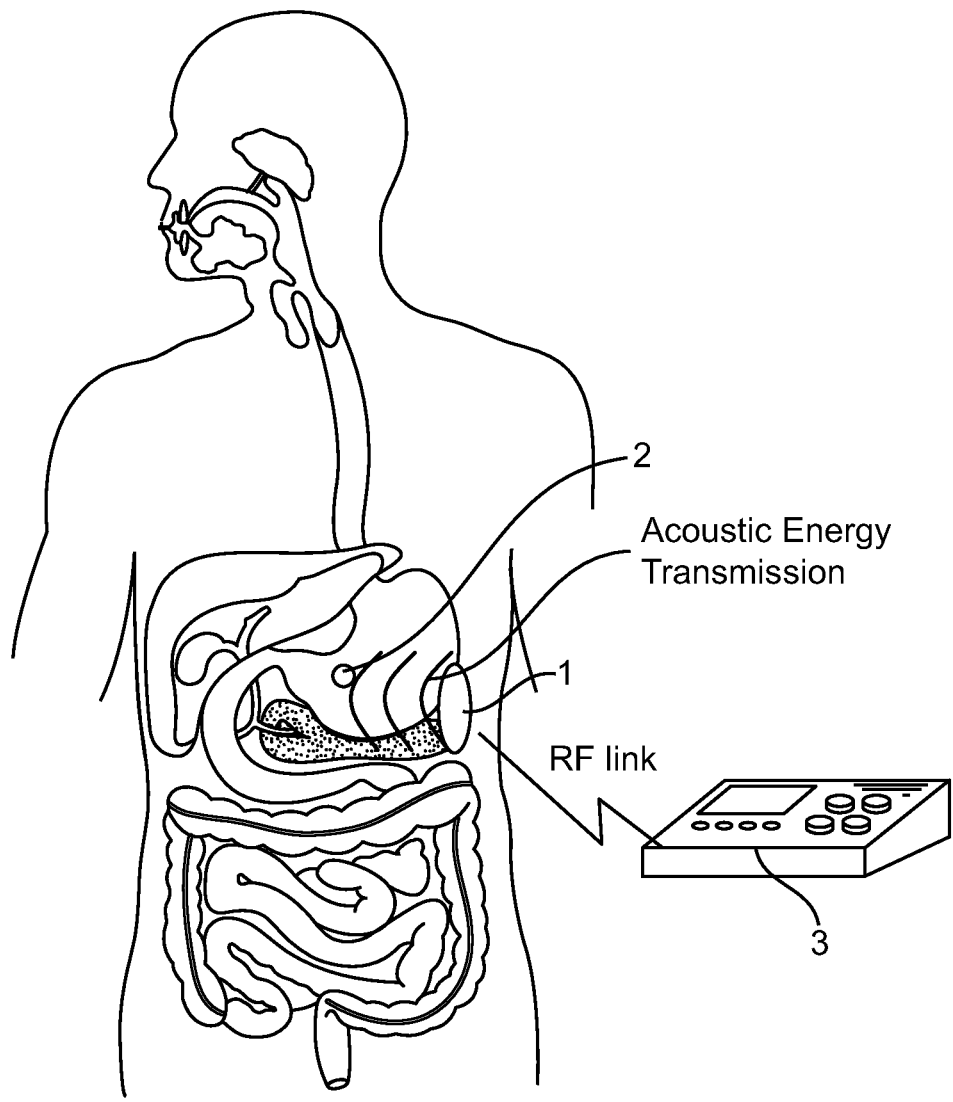
FIG. 2 is a schematic showing the leadless stimulation system in application with an implantable controller-transmitter for stimulation of the stomach.
Figure 3:
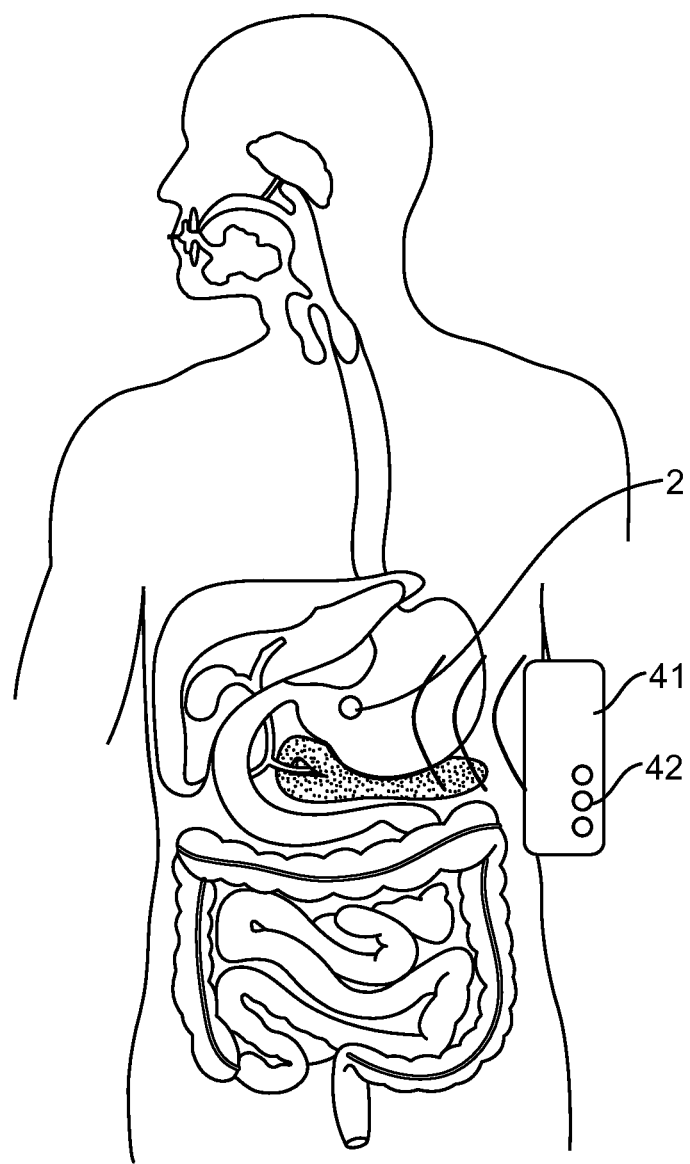
FIG. 3 is a schematic showing the leadless stimulation system in application with an externally applied controller-transmitter for stimulation of the stomach.

Examples of such an electro-acoustic stimulation system as a gastrointestinal tissue stimulator are illustrated in FIGS. 2 and 3.

In FIG. 2, a controller-transmitter device 1 containing circuitry to provide stimulation control and ultrasound transmission, plus means to communicate with an outside programmer 3 is implanted subcutaneously. It is situated such that the directional angle of the transmitted ultrasound beam would intersect the receiver-stimulator 2. An ultrasound signal is transmitted by this device through intervening body tissue to the receiver-stimulator device 2 containing means to receive this acoustic energy and convert it into an electrical waveform which may then be applied to the attached electrodes. In FIG. 2 this receiver-stimulator device 2 is shown embedded, in this one example, in the pylorus region of the stomach. The receiver-stimulator device 2 is shown here as a small cylindrical or button-shaped device placed on the gastrointestinal tissue in similar ways that current stimulator systems apply electrodes to stomach tissues. Optionally, the receiver-stimulator 2 could be deployed onto the gastrointestinal tissue or in proximity to the gastrointestinal tissue affixed with an attaching coil or other method. Also optionally (not shown), the receiver-stimulator device 2 could be incorporated into a expandable or self-expanding mechanical mesh that would stay located in the gastrointestinal tissue by means of spring tension similar to a stent placement in a vascular application but rather held in place between gastrointestinal tissue sections near the gastrointestinal tissue.

In FIG. 3, an externally applied controller-transmitter device 41 containing circuitry to provide stimulation therapy control and ultrasound transmission, plus control means 42 to allow the patient or operator to directly adjust ultrasound output based on desired therapy parameters including at least amplitude, pulse duration, and pulse repetition frequency, to produce an effective control of the gastrointestinal tissue. The external transmitter 41 may be handheld, or worn on the body, attached by a belt, harness, or the like. The external controller-transmitter 41 is similar to the implantable controller-transmitter device described previously, containing at the minimum an adjustable pulse/frequency generator, ultrasound amplifier, ultrasound transmitter, and battery. Optionally, the battery may be a rechargeable type. It is situated such that the directional angle of the transmitted ultrasound beam would intersect the receiver-stimulator 2. An ultrasound signal is transmitted by this device through intervening body tissue to the receiver-stimulator device 2 containing means to receive this acoustic energy and convert it into an electrical waveform which may then be applied to the attached electrodes. In FIG. 3, this receiver-stimulator device 2 is shown embedded, in this one example, in the pylorus region of the stomach and could be used with appropriate selection of stimulation parameters for obesity treatment.

Figure 4:
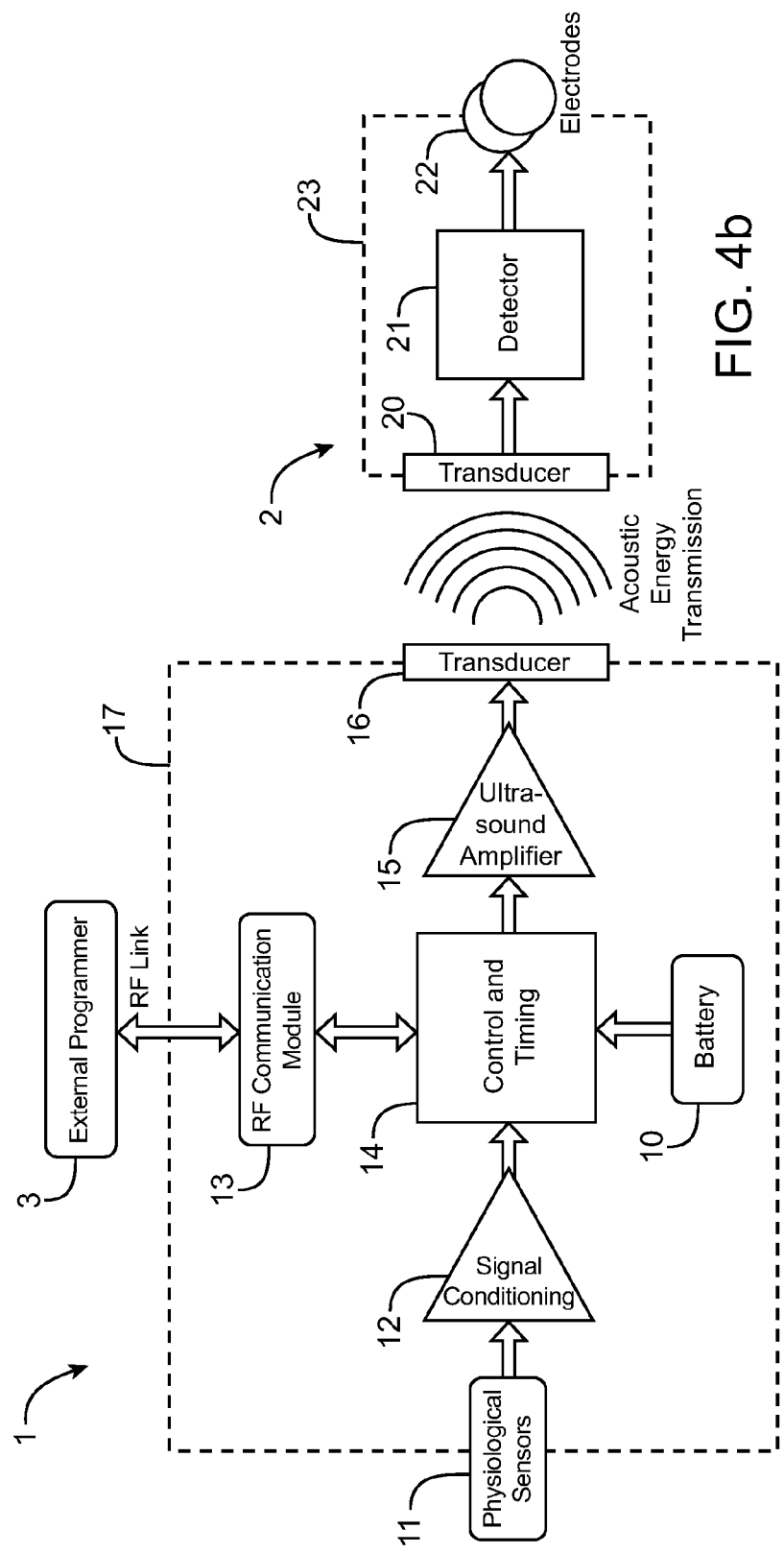
FIGS. 4a and 4b are block diagrams showing the components of the acoustic controller-transmitter and acoustic receiver-stimulators of the present invention.

FIGS. 4a and 4b show more details of the system described above and shown in FIG. 2. In FIG. 4a the controller-transmitter device 1 comprises: a battery 10, one or more sensors 11, signal processing circuitry 12, a communications module 13, a control and timing module 14, an ultrasound amplifier 15, and an ultrasound transducer 16. The battery 10 which provides power for the controller-transmitter may be of a type commonly used in implanted medical devices such as a lithium iodine cell or lithium silver vanadium oxide cell made by Greatbatch, Inc. or which is optionally a rechargeable battery. One or more sensors 11 are used to detect physiological parameters. Suitable sensors are known for the detection of electrical activity, temperature, motion, strain, pressure, and the like. The one or more sensors 11 are used to detect physiological parameters. Sensors may be chosen to measure acute response or to measure chronic progression of response. These sensors being connected to signal processing circuitry 12 and optionally used by the circuitry to adjust delivery of stimulation therapy or to communicate diagnostic information from the sensors. The communications module 13 provides a data path to allow the physician to set device parameters and to acquire diagnostic information about the patient and/or the device. The data path may be by an RF communication link, magnetic coupling, ultrasound pulses, or the like, and would communicate to and from an external unit 3. Device parameters would be used by the control and timing module 14. Device parameters would include adjustments to transmissions, such as power amplitude, pulse duration, duty cycle, and the like. The control and timing module 14 uses device parameters in conjunction with the acquired physiological data to generate the required control signals for the ultrasound amplifier 15 which in turn applies electrical energy to the ultrasound transducer 16 which in turn produces the desired acoustic beam. The controller-transmitter device 1 is encased in a hermetically sealed case 17 constructed of a biologically compatible material, similar to currently existing GTS devices.

Figure 5:
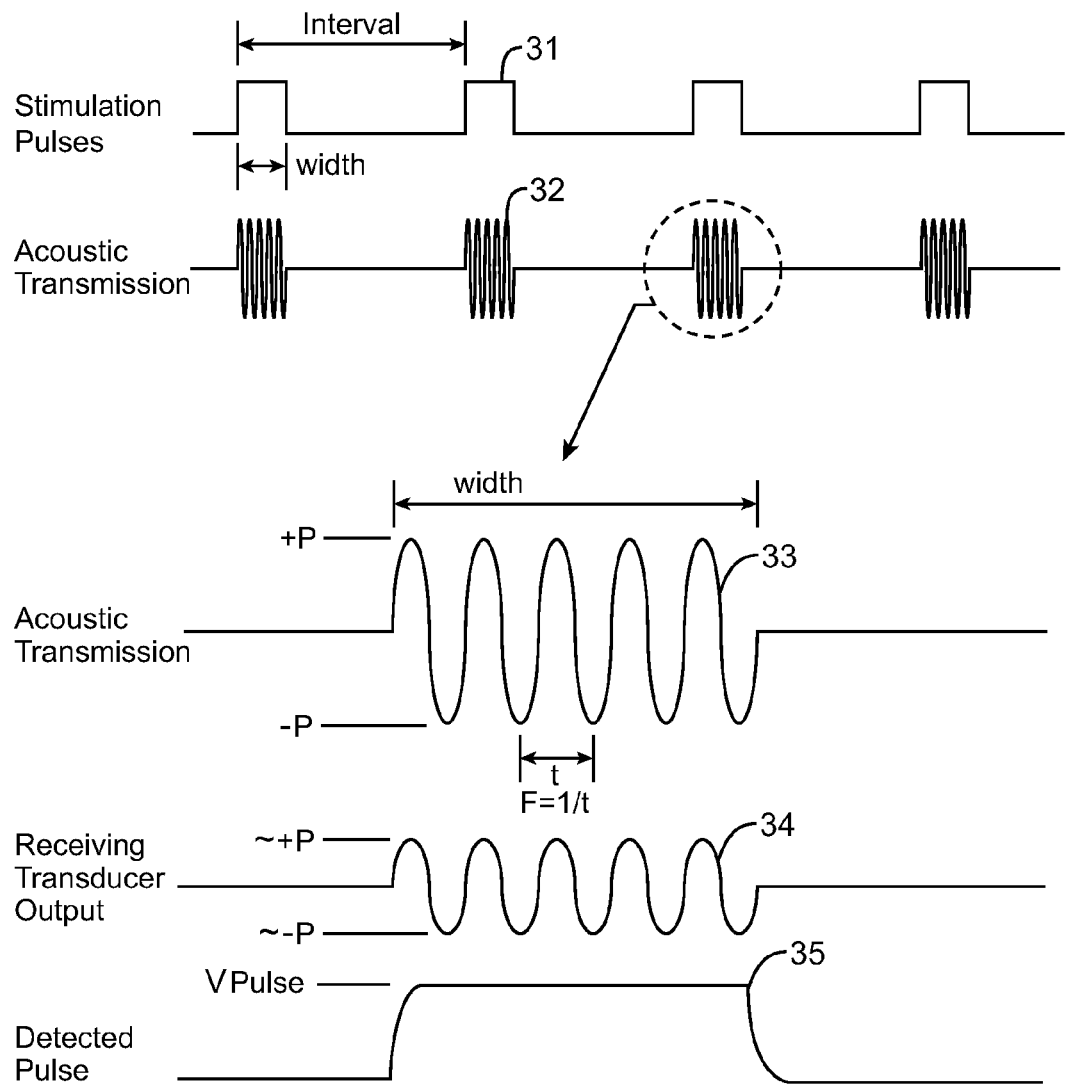
FIG. 5 illustrates representative acoustic and electrical signals useful in the systems and methods of the present invention.

Referring to FIG. 4b, the receiver-stimulator device 2, implanted in the path of the acoustic beam at the location where electrical stimulation is desired, contains an ultrasound transducer 20, an electrical circuit 21, and electrodes 22. Ultrasound transducer 20, typically made of a piezoelectric ceramic material, a piezoelectric single crystal, or piezoelectric polymer or copolymer films, intercepts a portion of the transmitted acoustic energy and converts it into an electrical current waveform from the original alternating nature of the applied ultrasound pressure wave. This electrical signal is applied to an electrical circuit 21 which may be one of a type commonly known as an envelope detector, and which may have one of many known circuit configurations, for example a full-wave rectifier, a half-wave rectifier, a voltage doubler or the like. Electrical circuit 21 produces a voltage pulse with amplitude proportional to the amplitude of the transmitted ultrasound burst and with a pulse length generally equal to the length of the transmitted burst. The circuit 21 may also have different configurations and functions, and provide output signals having characteristics other than a pulse. This signal is applied then to electrodes 22 which are typically made of platinum, platinum-iridium, gold, or the like. These may be incorporated onto the outer surface of the device, and thus in direct contact with gastrointestinal tissues or in close proximity to gastrointestinal tissues which are to be treated by stimulation. Alternatively, the electrodes 22 are connected via wires to a main body that consists of the transducer 20 and electrical circuit 21 and the electrodes 22 are adapted to be shapeable, malleable configurations that conform to the gastrointestinal tissue as flexible wraps or the like or that could be placed on the outside of the gastrointestinal tissue. Electrodes may be adapted that are round, long, segmented, etc. to increase surface area or to control current density at the electrode. Electrodes may be placed within the gastrointestinal tubular structure or on opposing sides of the gastrointestinal tissue or in linear alignment with the gastrointestinal tissue or in any arrangement suitable for the size and location of the gastrointestinal tissue and the targeted gastrointestinal tissue stimulation site. The receiver-stimulator device 2 is also enclosed within a sealed case 23 of biologically compatible material Referring also to previously described FIGS. 4a and 4b, FIG. 5 provides detail representing exemplary acoustic and electrical signals of the present system. FIG. 5 first depicts a train of electrical stimulation pulses 31 which have a desired width and are repeated at a desired interval. The controller-transmitter device 1 produces acoustic transmissions 32, for the desired stimulation pulse width and repeated at the desired stimulation pulse interval, which are emitted from the ultrasound transducer 16. Below the waveform 32 is shown an enlargement 33 of a single acoustic burst. This burst again has a desired width, a desired oscillation frequency F=1/t, and also a desired acoustic pressure indicated by the peak positive pressure P+ and peak negative pressure P−. The acoustic pressure wave, when striking the receiving transducer 20 of the receiver-stimulator device 2 generates an electrical signal 34 having frequency and burst length matching that of the transmitted waveform 33 and amplitude proportional to the transmitted acoustic pressure (~+/−P). This electrical waveform is then rectified and filtered by the circuit 21 producing the desired pulse 35 with length equal to the burst length of the transmitted waveform 33 and amplitude (VPULSE) proportional to the amplitude of the electrical signal 34. Thus, it can be seen that it is possible in this example to vary the stimulation rate by varying the time between ultrasound bursts, to vary the duration of any one stimulation pulse by varying the duration of the ultrasound burst, and to vary the amplitude of the stimulation pulse by varying the amplitude of the transmitted ultrasound waveform. Circuit 21 could be configured to produce a direct current (DC) output or an alternating current (AC) output, or an output with any arbitrary waveform. Varying the use of signal information within the ultrasound transmission for pulse duration, pulse amplitude, and duty cycle would result in any type of burst sequencing or continuous delivery waveform effective for gastrointestinal tissue stimulation. Using signal information in the ultrasound transmission the resultant waveshape may be a square wave, triangle wave, biphasic wave, multi-phase wave, or the like.

In practice, the amount of acoustic energy received by the implanted receiver-stimulator device will vary with ultrasound attenuation caused by loss in the intervening body tissue, with spatial location of the receiver-stimulator device with respect to the transmitted ultrasound beam as such a beam is typically non-uniform from edge-to-edge, and possibly with orientation (rotation) of the receiver-stimulator device with respect to the first. Such variation would affect the amplitude of the stimulating pulse for a given ultrasound transmit power (acoustic pressure amplitude). This limitation can be overcome by adjusting the ultrasound transmit power until the resultant stimulation waveform is consistent, a technique similar to that used currently to determine stimulation thresholds at the time of cardiac pacemaker implantation. Another approach would be to adjust automatically using sensing and logic within the first device. The first device would periodically sense the electrical output of the receiver-stimulator device and adjust power transmission accordingly to compensate for any change in the system including relative movement between the transmitting and receiving devices. Yet another embodiment for overcoming this limitation is where the transducer incorporated into the receiver-stimulator device is omni-directional in its reception capability. For example, to improve omni-directional sensitivity, the transducer may be spherical in shape or have specific dimensional characteristics relative to the wavelength of the transmitted ultrasound. Alternatively, multiple transducers are disposed at appropriate angles to reduce or eliminate the directional sensitivity of the device.

Figure 6A:
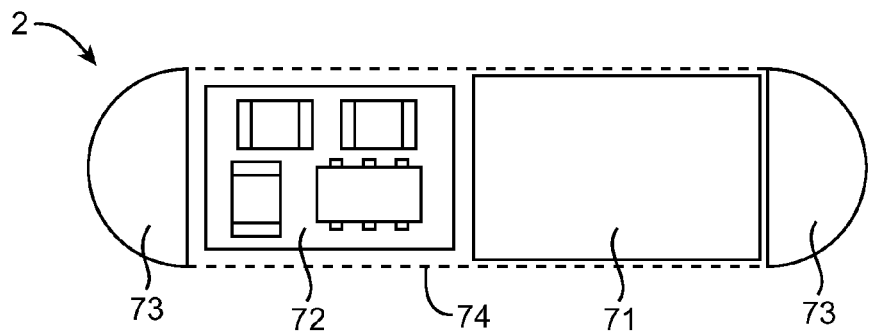
FIGS. 6a, 6b, and 6c are schematic illustrations showing components of the present invention.
Figure 6B:
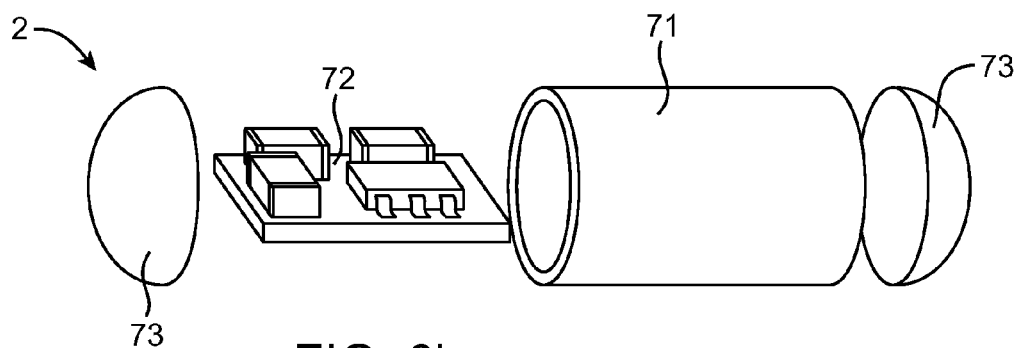
Figure 6C:
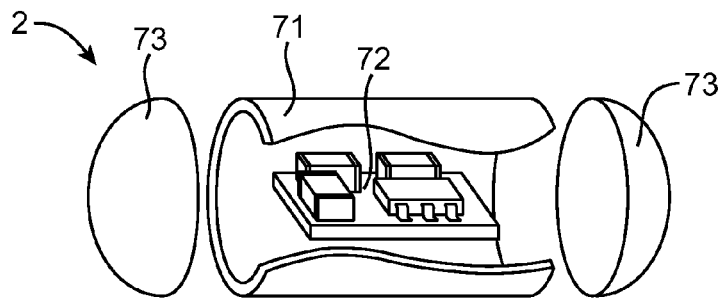

FIGS. 6a through 6c illustrate two embodiments of a small implantable receiver-stimulator of a cylindrical profile, suitable perhaps for placement by stylet or by injection through a hypodermic needle. FIG. 6a shows in plan view and 6b in perspective view such a receiver-stimulator 2 having a hollow, cylindrical ultrasound transducer 71, a circuit assembly 72 comprising the detector, and two electrodes 73 at either end of the assembly. It can be appreciated that any number of electrodes may be adapted to this embodiment. The transducer 71 would be made of an appropriate piezoelectric ceramic or single crystal material, having two electrical activity contacts deposited on the outer and inner surfaces of the cylinder, respectively. The transducer and circuit would be encapsulated in an electrically insulating but acoustically transparent medium 74. The transducer 71 would be of a rigid piezoelectric material, typically a piezo-ceramic with electrodes deposited on the outer and inner surfaces of the cylinder. The circuit assembly 72 may be fabricated using known surface-mount or hybrid assembly techniques, upon either a fiberglass or ceramic substrate. Stimulation electrodes 73 would be fabricated of material commonly used in implanted electrodes, such as platinum, platinum-iridium, or the like. Necessary electrical wiring between the transducer, circuit board, and electrodes is not shown in these drawings. Typical dimensions of such a device would be 1.5 cm in length and 1.5 mm in diameter, and preferably smaller. Multiple electrodes could be adapted as appendages to the embodiment (not shown) or incorporated into fixation elements such as helical screws, clips, or barbs (not shown).

As shown in FIG. 6c, by using hybrid circuit techniques it may be possible to further miniaturize the circuit assembly 72 such that it would fit inside the hollow interior of the transducer 71. This would have the benefit of substantially reducing the length of the finished device.

While exemplary embodiments have been shown and described in detail for purposes of clarity, it will be clear to those of ordinary skill in the art from a reading of the disclosure that various changes in form or detail, modifications, or other alterations to the invention as described may be made without departing from the true scope of the invention in the appended claims. For example, while specific dimensions and materials for the device have been described, it should be appreciated that changes to the dimensions or the specific materials comprising the device will not detract from the inventive concept. Accordingly, all such changes, modifications, and alterations should be seen as within the scope of the disclosure.

What is claimed is:

1. A system for gastrointestinal tissue stimulation therapy, said system comprising:

an acoustic controller-transmitter configured to transmit acoustic energy wherein the controller-transmitter comprises acoustic transducers disposed in a housing and one or more sensors disposed on an external surface of the housing, and wherein the one or more sensors are configured to detect an electrical stimulation output and wherein the acoustic energy contains both energy and signal information; and an implantable acoustic receiver-stimulator having a stimulation electrode assembly adapted to be in direct contact with gastrointestinal tissue, wherein the receiver-stimulator is configured to receive and convert the acoustic energy into the electrical stimulation output delivered to the gastrointestinal tissue by the stimulation electrode assembly;

wherein the controller-transmitter is configured to sense the electrical stimulation output of the receiver-stimulator using one or more of the sensors; and adjust energy transmission accordingly in order to compensate for changes in electrical stimulation output of the receiver-stimulator.

2. The system as in claim 1, wherein the receiver-stimulator comprises an acoustic receiver which receives acoustic energy and generates alternating current, means for converting the alternating current to a pre-determined waveform, and the stimulation electrode assembly adapted to deliver the pre-determined waveform to stimulate the gastrointestinal tissue.

3. The system as in claim 2, wherein the implantable receiver-stimulator is adapted to be located in close proximity to the gastrointestinal tissue stimulation site.

4. The system as in claim 2, wherein the implantable receiver-stimulator is adapted to be located at a predetermined gastrointestinal tissue stimulation site, and stimulate the gastrointestinal tissue site for achieving a therapeutic effect, wherein said predetermined gastrointestinal tissue stimulation site is selected for treating one or more medical conditions chosen from the list comprising eating disorders, gastroparesis, and gastric reflux.

5. The system as in claim 1, wherein the controller-transmitter comprises a power source, control and timing circuitry to provide a stimulation signal, means for converting the stimulation signal to an acoustic energy signal, and means for transmitting the acoustic energy signal to the receiver-stimulator.

6. The system as in claim 5, wherein the controller-transmitter is adapted to be implantable.

7. The system as in claim 5, wherein control circuitry includes one or more means for sensing physiologic variables in order to adjust stimulation with one or more parameters chosen from pulse amplitude, pulse duration, duty cycle, or timing.

8. The system as in anyone of claims 3-5, further comprising at least one additional receiver-stimulator device.

9. The system as in claim 8, wherein, the system is programmed to activate the receiver-stimulator devices sequentially.

10. The system as in claim 8, wherein the system is programmed to activate the receiver-stimulator devices simultaneously.

11. The system as in claim 1, adapted to transmit and receive acoustic energy wherein the frequency of the acoustic energy is between 20 kHz and 10 MHz, the burst length is between 3 cycles and a continuous burst, the duty cycle is between 0.01% and 100.00%, and the mechanical index is less than 1.9.

* * * * *